United States Patent
Stahmann et al.

(10) Patent No.: US 6,871,095 B2
(45) Date of Patent: Mar. 22, 2005

(54) METHOD AND APPARATUS FOR MAINTAINING SYNCHRONIZED PACING

(75) Inventors: Jeffrey E. Stahmann, Ramsey, MN (US); Andrew P. Kramer, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 4 days.

(21) Appl. No.: 10/353,175

(22) Filed: Jan. 27, 2003

(65) Prior Publication Data

US 2003/0149454 A1 Aug. 7, 2003

Related U.S. Application Data

(63) Continuation of application No. 09/748,794, filed on Dec. 26, 2000, now Pat. No. 6,512,952.

(51) Int. Cl.[7] ............................................. A61N 1/362
(52) U.S. Cl. ....................................................... 607/9
(58) Field of Search ........................................ 607/1–28

(56) References Cited

U.S. PATENT DOCUMENTS

| | | | |
|---|---|---|---|
| 4,343,311 A | 8/1982 | Markowitz | 128/419 PG |
| 4,354,497 A | 10/1982 | Kahn | 128/419 D |
| 4,686,989 A | 8/1987 | Smyth et al. | 128/419 PG |
| 4,779,617 A | 10/1988 | Whigham | 128/419 P |
| 4,928,688 A | 5/1990 | Mower | 128/419 PG |
| 4,974,589 A | 12/1990 | Sholder | 128/419 PG |
| 5,103,820 A | 4/1992 | Markowitz | 128/419 OPG |
| 5,123,412 A | 6/1992 | Betzold | 128/419 PG |
| 5,129,393 A | 7/1992 | Brumwell | 128/419 PG |
| 5,156,149 A | 10/1992 | Hudrlik | 128/419 PG |
| 5,174,289 A | 12/1992 | Cohen | 128/419 PG |
| 5,191,884 A | 3/1993 | Gilli et al. | 127/419 |
| 5,233,985 A | 8/1993 | Hudrlik | 607/27 |
| 5,267,560 A | 12/1993 | Cohen | 607/25 |
| 5,370,665 A | 12/1994 | Hudrlik | 607/9 |
| 5,507,782 A | 4/1996 | Kieval et al. | 607/9 |
| 5,514,161 A | 5/1996 | Limousin | 607/9 |
| 5,558,097 A | 9/1996 | Jacobson et al. | 128/705 |
| 5,584,867 A | 12/1996 | Limousin et al. | 607/9 |
| 5,653,738 A | 8/1997 | Sholder | 607/14 |
| 5,674,259 A | 10/1997 | Gray | 607/20 |
| 5,792,183 A | 8/1998 | Esler | 607/4 |
| 5,792,203 A | 8/1998 | Schroeppel | 607/30 |
| 5,797,970 A | 8/1998 | Pouvreau | 607/9 |
| 5,902,324 A | 5/1999 | Thompson et al. | 607/9 |
| 5,935,160 A | 8/1999 | Auricchio et al. | 607/122 |
| 5,941,830 A | 8/1999 | Williams | 600/509 |
| 6,070,101 A | 5/2000 | Struble et al. | 607/9 |
| 6,081,748 A | 6/2000 | Struble et al. | 607/9 |
| 6,122,545 A | 9/2000 | Struble et al. | 607/9 |
| 6,128,535 A | 10/2000 | Maarse | 607/28 |
| 6,169,918 B1 | 1/2001 | Haefner et al. | 600/509 |
| 6,188,926 B1 | 2/2001 | Vock | 607/9 |
| 6,240,313 B1 | 5/2001 | Esler | 600/516 |
| 6,263,242 B1 | 7/2001 | Mika | 607/9 |
| 6,285,907 B1 | 9/2001 | Kramer et al. | 607/9 |
| 6,317,631 B1 | 11/2001 | Ben-Haim et al. | 607/9 |
| 6,370,430 B1 | 4/2002 | Mika et al. | 607/9 |
| 6,411,848 B2 | 6/2002 | Kramer et al. | 607/9 |
| 6,421,564 B1 | 7/2002 | Yerich et al. | 607/9 |
| 6,424,866 B2 | 7/2002 | Mika et al. | 607/9 |
| 6,427,084 B2 | 7/2002 | Baker et al. | 607/9 |
| 6,438,421 B1 | 8/2002 | Stahmann et al. | 607/9 |

(List continued on next page.)

Primary Examiner—Scott M. Getzow
(74) Attorney, Agent, or Firm—Schwegman, Lundberg, Woessner & Kluth, P.A.

(57) ABSTRACT

A device and method for cardiac rhythm management in which a cardiac site is paced in accordance with a pacing mode that employs sense signals from a different cardiac site. A protective period triggered by the sensing of intrinsic activity at the paced site is used to delay pacing by a protective delay interval without otherwise disturbing the pacing algorithm.

20 Claims, 3 Drawing Sheets

U.S. PATENT DOCUMENTS

| | | | |
|---|---|---|---|
| 6,456,878 B1 | 9/2002 | Yerich et al. | 607/9 |
| 6,456,880 B1 | 9/2002 | Park et al. | 607/25 |
| 6,466,820 B1 | 10/2002 | Juran et al. | 607/9 |
| 6,477,415 B1 | 11/2002 | Yerich et al. | 607/9 |
| 6,477,417 B1 | 11/2002 | Levine | 607/9 |
| 6,496,730 B1 | 12/2002 | Kleckner et al. | 607/9 |
| 6,501,988 B2 | 12/2002 | Kramer et al. | 607/9 |
| 6,512,953 B2 | 1/2003 | Florio et al. | 607/28 |
| 6,522,921 B2 | 2/2003 | Stahmann et al. | 607/9 |
| 6,522,923 B1 | 2/2003 | Turcott | 607/27 |
| 6,553,259 B2 | 4/2003 | Mouchawar et al. | 607/11 |
| 6,628,988 B2 | 9/2003 | Kramer et al. | 607/9 |
| 2002/0082655 A1 | 6/2002 | Kramer et al. | 607/9 |

METHOD AND APPARATUS FOR MAINTAINING SYNCHRONIZED PACING

CROSS-REFERENCE TO RELATED APPLICATION(S)

This application is a continuation of U.S. application Ser. No. 09/748,794, filed on Dec. 26, 2000 now U.S. Pat. No. 6,512,952, the specification of which is incorporated herein by reference.

FIELD OF THE INVENTION

This invention pertains to methods and apparatus for cardiac rhythm management. In particular, the invention relates to methods and apparatus for providing ventricular resynchronization therapy.

BACKGROUND

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are fixed or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Pacing therapy may also be applied in order to treat cardiac rhythms that are too fast, termed anti-tachycardia pacing. (As the term is used herein, a pacemaker is any cardiac rhythm management device with a pacing functionality, regardless of any other functions it may perform such as cardioversion or defibrillation.)

Also included within the concept of cardiac rhythm is the degree to which the heart chambers contract in a coordinated manner during a cardiac cycle to result in the efficient pumping of blood. The heart has specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Patients who exhibit pathology of these conduction pathways, such as bundle branch blocks, can thus suffer compromised cardiac output.

Patients with conventional pacemakers can also have compromised cardiac output because artificial pacing with an electrode fixed into an area of the myocardium does not take advantage of the above-described specialized conduction system. This is because the specialized conduction system can only be entered by impulses emanating from the sino-atrial or atrio-ventricular nodes. The spread of excitation from a single pacing site must proceed only via the much slower conducting muscle fibers of either the atria or the ventricles, resulting in the part of the myocardium stimulated by the pacing electrode contracting well before parts of the chamber located more distally to the electrode, including the myocardium of the chamber contralateral to the pacing site. Although the pumping efficiency of the heart is somewhat reduced from the optimum, most patients can still maintain more than adequate cardiac output with artificial pacing.

Heart failure is clinical syndrome in which an abnormality of cardiac function causes cardiac output to fall below a level adequate to meet the metabolic demand of peripheral tissues and is usually referred to as congestive heart failure (CHF) due to the accompanying venous and pulmonary congestion. CHF can be due to a variety of etiologies with ischemic heart disease being the most common. Some CHF patients suffer from some degree of AV block or are chronotropically deficient such that their cardiac output can be improved with conventional bradycardia pacing. Such pacing, however, may result in some degree of uncoordination in atrial and/or ventricular contractions due to the way in which pacing excitation is spread throughout the myocardium as described above. The resulting diminishment in cardiac output may be significant in a CHF patient whose cardiac output is already compromised. Intraventricular and/or interventricular conduction defects (e.g., bundle branch blocks) are also commonly found in CHF patients. In order to treat these problems, cardiac rhythm management devices have been developed which provide pacing stimulation to one or more heart chambers in an attempt to improve the coordination of atrial and/or ventricular contractions, termed cardiac resynchronization therapy.

SUMMARY OF THE INVENTION

Cardiac resynchronization therapy can most conveniently be delivered by a cardiac rhythm management device in accordance with a bradycardia pacing mode so that the selected heart chambers are both resynchronized and paced simultaneously. One heart chamber, designated as the rate chamber, is paced with the bradycardia mode while the the contralateral chamber, designated as the synchronized chamber, is paced with a synchronized mode based upon senses and paces occurring in the rate chamber. In order to protect the synchronized chamber from being paced near the time of an intrinsic contraction and within its vulnerable period, a synchronized chamber protection period is initiated by a sense or pace in the chamber which inhibits any scheduled synchronized pace.

In order for cardiac resynchronization therapy to be effective, resynchronization pacing pulses should be delivered as often as possible. The present invention is directed toward a method that attempts to maintain resynchronization pacing when it would otherwise be inhibited by the synchronized chamber protective period. Accordingly, a pace to the synchronized chamber is delayed by a protective delay interval when the scheduled pace would otherwise occur within the synchronized chamber protection period.

DESCRIPTION OF THE INVENTION

Cardiac resynchronization therapy may involve pacing a heart chamber designated as the synchronized chamber in accordance with a pacing mode based upon intrinsic activity in the contralateral chamber, designated as the rate chamber. This presents risks because a chamber is being paced without the benefit of a sense signal from that chamber triggering the pace or causing an escape interval to be reset so that no pace is delivered. In order to help prevent the synchronized chamber from receiving a pace near the time of an intrinsic beat and within the chamber's vulnerable period, a synchronized chamber protection period may be initiated upon a synchronized chamber pace or sense that inhibits pacing of the synchronized chamber for the duration of the period. The disadvantage of this scheme, however, is that the benefit of resynchronization therapy is lost for any cardiac cycle in which the synchronized pace is inhibited. The present invention provides a means for maintaining resynchronization therapy during certain of these inhibited cycles by delaying the scheduled pacing instant for the synchronized chamber pace for a protective delay interval when it would otherwise fall with the synchronized chamber protection period.

1. Hardware Platform

Pacemakers are typically implanted subcutaneously on a patient's chest and have leads threaded intravenously into the heart to connect the device to electrodes used for sensing and pacing. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the chamber.

Figure 1:
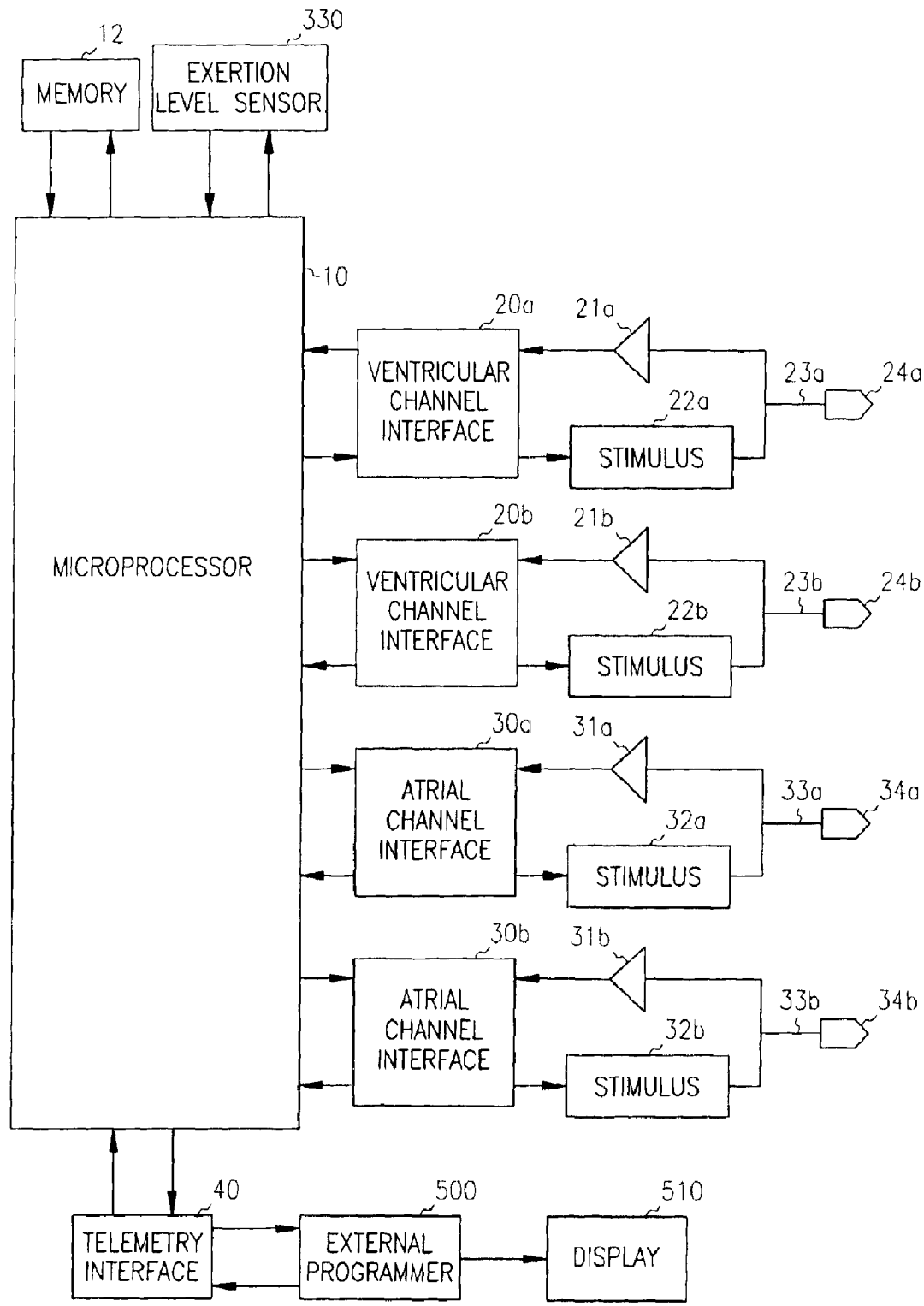
FIG. 1 is a system diagram of a pacemaker configured for biventricular pacing and sensing.

FIG. 1 shows a system diagram of a microprocessor-based pacemaker physically configured with sensing and pacing channels for both atria and both ventricles. The controller 10 of the pacemaker is a microprocessor which communicates with a memory 12 via a bidirectional data bus. The memory 12 typically comprises a ROM (read-only memory) for program storage and a RAM (random-access memory) for data storage. The pacemaker has atrial sensing and pacing channels comprising electrode 34a–b, leads 33a–b, sensing amplifiers 31a–b, pulse generators 32a–b, and atrial channel interfaces 30a–b which communicate bidirectionally with microprocessor 10. The device also has ventricular sensing and pacing channels for both ventricles comprising electrodes 24a–b, leads 23a–b, sensing amplifiers 21a–b, pulse generators 22a–b, and ventricular channel interfaces 20a–b. In the figure, "a" designates one ventricular or atrial channel and "b" designates the channel for the contralateral chamber. In this embodiment, a single electrode is used for sensing and pacing in each channel, known as a unipolar lead. Other embodiments may employ bipolar leads which include two electrodes for outputting a pacing pulse and/or sensing intrinsic activity. The channel interfaces 20a–b and 30a–b include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. An exertion level sensor 330 (e.g., an accelerometer or a minute ventilation sensor) enables the controller to adapt the pacing rate in accordance with changes in the patient's physical activity. A telemetry interface 40 is also provided for communicating with an external programmer 500 which has an associated display 510. A pacemaker incorporating the present invention may possess all of the components in FIG. 1 and be programmable so as to operate in a number of different modes, or it may have only those components necessary to operate in a particular mode.

The controller 10 controls the overall operation of the device in accordance with programmed instructions stored in memory. The controller 10 controls the delivery of paces via the pacing channels, interprets sense signals from the sensing channels, implements timers for defining escape intervals and sensory refractory periods, and performs the pace counting functions as described below. It should be appreciated, however, that these functions could also be performed by custom logic circuitry either in addition to or instead of a programmed microprocessor.

2. Bradycardia Pacing Modes

Bradycardia pacing modes refer to pacing algorithms used to pace the atria and/or ventricles when the intrinsic ventricular rate is inadequate either due to AV conduction blocks or sinus node dysfunction. Such modes may either be single-chamber pacing, where either an atrium or a ventricle is paced, or dual-chamber pacing in which both an atrium and a ventricle are paced. The modes are generally designated by a letter code of three positions where each letter in the code refers to a specific function of the pacemaker. The first letter refers to which heart chambers are paced and which may be an A (for atrium), a V (for ventricle), D (for both chambers), or O (for none). The second letter refers to which chambers are sensed by the pacemaker's sensing channels and uses the same letter designations as used for pacing. The third letter refers to the pacemaker's response to a sensed P wave from the atrium or an R wave from the ventricle and may be an I (for inhibited), T (for triggered), D (for dual in which both triggering and inhibition are used), and O (for no response). Modern pacemakers are typically programmable so that they can operate in any mode which the physical configuration of the device will allow. Additional sensing of physiological data allows some pacemakers to change the rate at which they pace the heart in accordance with some parameter correlated to metabolic demand. Such pacemakers are called rate-adaptive pacemakers and are designated by a fourth letter added to the three-letter code, R.

Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat and during the heart's vulnerable period which may cause fibrillation. Most pacemakers for treating bradycardia today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker. Such an escape interval can be defined for each paced chamber. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL).

In atrial tracking pacemakers (i.e., VDD or DDD mode), another ventricular escape interval is defined between atrial and ventricular events, referred to as the atrio-ventricular interval (AVI). The atrio-ventricular interval is triggered by an atrial sense or pace and stopped by a ventricular sense or pace. A ventricular pace is delivered upon expiration of the atrio-ventricular interval if no ventricular sense occurs before. Atrial-tracking ventricular pacing attempts to maintain the atrio-ventricular synchrony occurring with physiological beats whereby atrial contractions augment diastolic filling of the ventricles. If a patient has a physiologically normal atrial rhythm, atrial-tracking pacing also allows the ventricular pacing rate to be responsive to the metabolic needs of the body.

A pacemaker can also be configured to pace the atria on an inhibited demand basis. An atrial escape interval is then defined as the maximum time interval in which an atrial sense must be detected after a ventricular sense or pace before an atrial pace will be delivered. When atrial inhibited demand pacing is combined with atrial-triggered ventricular demand pacing (i.e., DDD mode), the lower rate interval is then the sum of the atrial escape interval and the atrio-ventricular interval.

Another type of synchronous pacing is atrial-triggered or ventricular-triggered pacing. In this mode, an atrium or ventricle is paced immediately after an intrinsic beat is detected in the respective chamber. Triggered pacing of a heart chamber is normally combined with inhibited demand pacing so that a pace is also delivered upon expiration of an escape interval in which no intrinsic beat occurs. Such triggered pacing may be employed as a safer alternative to asynchronous pacing when, due to far-field sensing of electromagnetic interference from external sources or skeletal muscle, false inhibition of pacing pulses is a problem. If a sense in the chamber's sensing channel is an actual depolarization and not a far-field sense, the triggered pace is delivered during the chamber's physiological refractory period and is of no consequence.

Finally, rate-adaptive algorithms may be used in conjunction with bradycardia pacing modes. Rate-adaptive pacemakers modulate the ventricular and/or atrial escape intervals based upon measurements corresponding to physical activity. Such pacemakers are applicable to situations in which atrial tracking modes cannot be use. In a rate-adaptive pacemaker operating in a ventricular pacing mode, the LRL is adjusted in accordance with exertion level measurements such as from an accelerometer or minute ventilation sensor in order for the heart rate to more nearly match metabolic demand. The adjusted LRL is then termed the sensor-indicated rate.

3. Cardiac Resynchronization Therapy

Cardiac resynchronization therapy is pacing stimulation applied to one or more heart chambers in a manner that restores or maintains synchronized bilateral contractions of the atria and/or ventricles and thereby improves pumping efficiency. Certain patients with conduction abnormalities may experience improved cardiac synchronization with conventional single-chamber or dual-chamber pacing as described above. For example, a patient with left bundle branch block may have a more coordinated contraction of the ventricles with a pace than as a result of an intrinsic contraction. In that sense, conventional bradycardia pacing of an atrium and/or a ventricle may be considered as resynchronization therapy. Resynchronization pacing, however, may also involve pacing both ventricles and/or both atria in accordance with a synchronized pacing mode as described below. A single chamber may also be resynchronized to compensate for intra-atrial or intra-ventricular conduction delays by delivering paces to multiple sites of the chamber.

It is advantageous to deliver resynchronization therapy in conjunction with one or more synchronous bradycardia pacing modes, such as are described above. One atrial and/or one ventricular pacing sites are designated as rate sites, and paces are delivered to the rate sites based upon pacing and sensed intrinsic activity at the site in accordance with the bradycardia pacing mode. In a single-chamber bradycardia pacing mode, for example, one of the paired atria or one of the ventricles is designated as the rate chamber. In a dual-chamber bradycardia pacing mode, either the right or left atrium is selected as the atrial rate chamber and either the right or left ventricle is selected as the ventricular rate chamber. The heart rate and the escape intervals for the pacing mode are defined by intervals between sensed and paced events in the rate chambers only. Resynchronization therapy may then be implemented by adding synchronized pacing to the bradycardia pacing mode where paces are delivered to one or more synchronized pacing sites in a defined time relation to one or more selected sensing and pacing events that either reset escape intervals or trigger paces in the bradycardia pacing mode. Multiple synchronized sites may be paced through multiple synchronized sensing/pacing channels, and the multiple synchronized sites may be in the same or different chambers as the rate site.

In bilateral synchronized pacing, which may be either biatrial or biventricular synchronized pacing, the heart chamber contralateral to the rate chamber is designated as a synchronized chamber. For example, the right ventricle may be designated as the rate ventricle and the left ventricle designated as the synchronized ventricle, and the paired atria may be similarly designated. Each synchronized chamber is then paced in a timed relation to a pace or sense occurring in the contralateral rate chamber in accordance with a synchronized pacing mode as described below.

One synchronized pacing mode may be termed offset synchronized pacing. In this mode, the synchronized chamber is paced with a positive, negative, or zero timing offset as measured from a pace delivered to its paired rate chamber, referred to as the synchronized chamber offset interval. The offset interval may be zero in order to pace both chambers simultaneously, positive in order to pace the synchronized chamber after the rate chamber, or negative to pace the synchronized chamber before the rate chamber. One example of such pacing is biventricular offset synchronized pacing where both ventricles are paced with a specified offset interval. The rate ventricle is paced in accordance with a synchronous bradycardia mode which may include atrial tracking, and the ventricular escape interval is reset with either a pace or a sense in the rate ventricle. (Resetting in this context refers to restarting the interval in the case of an LRL ventricular escape interval and to stopping the interval in the case of an AVI.) Thus, a pair of ventricular paces are delivered after expiration of the AVI escape interval or expiration of the LRL escape interval, with ventricular pacing inhibited by a sense in the rate ventricle that restarts the LRL escape interval and stops the AVI escape interval. In this mode, the pumping efficiency of the heart will be increased in some patients by simultaneous pacing of the ventricles with an offset of zero. However, it may be desirable in certain patients to pace one ventricle before the other in order to compensate for different conduction velocities in the two ventricles, and this may be accomplished by specifying a particular positive or negative ventricular offset interval.

Another synchronized mode is triggered synchronized pacing. In one type of triggered synchronized pacing, the synchronized chamber is paced after a specified trigger interval following a sense in the rate chamber, while in another type the rate chamber is paced after a specified trigger interval following a sense in the synchronized chamber. The two types may also be employed simultaneously. For example, with a trigger interval of zero, pacing of one chamber is triggered to occur in the shortest time possible after a sense in the other chamber in order to produce a coordinated contraction. (The shortest possible time for the triggered pace is limited by a sense-to-pace latency period dictated by the hardware.) This mode of pacing may be desirable when the intra-chamber conduction time is long enough that the pacemaker is able to reliably insert a pace before depolarization from one chamber reaches the other. Triggered synchronized pacing can also be combined with offset synchronized pacing such that both chambers are paced with the specified offset interval if no intrinsic activity is sensed in the rate chamber and a pace to the rate chamber is not otherwise delivered as a result of a triggering event. A specific example of this mode is ventricular triggered synchronized pacing where the rate and synchronized chambers are the right and left ventricles, respectively, and a sense in the right ventricle triggers a pace to the left ventricle and/or a sense in the left ventricle triggers a pace to the right ventricle.

As with other synchronized pacing modes, the rate chamber in a triggered synchronized pacing mode can be paced with one or more synchronous bradycardia pacing modes. If the rate chamber is controlled by a triggered bradycardia mode, a sense in the rate chamber sensing channel, in addition to triggering a pace to the synchronized chamber, also triggers an immediate rate chamber pace and resets any rate chamber escape interval. The advantage of this modal combination is that the sensed event in the rate chamber sensing channel might actually be a far-field sense from the synchronized chamber, in which case the rate chamber pace should not be inhibited. In a specific example, the right and left ventricles are the rate and synchronized chambers, respectively, and a sense in the right ventricle triggers a pace to the left ventricle. If right ventricular triggered pacing is also employed as a bradycardia mode, both ventricles are paced after a right ventricular sense has been received to allow for the possibility that the right ventricular sense was actually a far-field sense of left ventricular depolarization in the right ventricular channel. If the right ventricular sense were actually from the right ventricle, the right ventricular pace would occur during the right ventricle's physiological refractory period and cause no harm.

As mentioned above, certain patients may experience some cardiac resynchronization from the pacing of only one ventricle and/or one atrium with a conventional bradycardia pacing mode. It may be desirable, however, to pace a single atrium or ventricle in accordance with a pacing mode based upon senses from the contralateral chamber. This mode, termed synchronized chamber-only pacing, involves pacing only the synchronized chamber based upon senses from the rate chamber. One way to implement synchronized chamber-only pacing is to pseudo-pace the rate chamber whenever the synchronized chamber is paced before the rate chamber is paced, such that the pseudo-pace inhibits a rate chamber pace and resets any rate chamber escape intervals. Such pseudo-pacing can be combined with the offset synchronized pacing mode using a negative offset to pace the synchronized chamber before the rate chamber and thus pseudo-pace the rate chamber, which inhibits the real scheduled rate chamber pace and resets the rate chamber pacing escape intervals. One advantage of this combination is that sensed events in the rate chamber will inhibit the synchronized chamber-only pacing, which may benefit some patients by preventing pacing that competes with intrinsic activation (i.e., fusion beats). Another advantage of this combination is that rate chamber pacing can provide backup pacing when in a synchronized chamber-only pacing mode, such that when the synchronized chamber pace is prevented, for example to avoid pacing during the chamber vulnerable period following a prior contraction, the rate chamber will not be pseudo-paced and thus will be paced upon expiration of the rate chamber escape interval. Synchronized chamber-only pacing can be combined also with a triggered synchronized pacing mode, in particular with the type in which the synchronized chamber is triggered by a sense in the rate chamber. One advantage of this combination is that sensed events in the rate chamber will trigger the synchronized chamber-only pacing, which may benefit some patients by synchronizing the paced chamber contractions with premature contralateral intrinsic contractions.

An example of synchronized chamber-only pacing is left ventricle-only synchronized pacing where the rate and synchronized chambers are the right and left ventricles, respectively. Left ventricle-only synchronized pacing may be advantageous where the conduction velocities within the ventricles are such that pacing only the left ventricle results in a more coordinated contraction by the ventricles than with conventional right ventricular pacing or biventricular pacing. Left ventricle-only synchronized pacing may be implemented in inhibited demand modes with or without atrial tracking, similar to biventricular pacing. A left ventricular pace is then delivered upon expiration of the AVI escape interval or expiration of the LRL escape interval, with left ventricular pacing inhibited by a right ventricular sense that restarts the LRL escape interval and stops the AVI escape interval.

In the synchronized modes described above, the rate chamber is synchronously paced with a mode based upon detected intrinsic activity in the rate chamber, thus protecting the rate chamber against paces being delivered during the vulnerable period. In order to provide similar protection to a synchronized chamber or synchronized pacing site, a synchronized chamber protection period (SCPP) may be provided. (In the case of multi-site synchronized pacing, a similar synchronized site protection period may be provided for each synchronized site.) The SCPP is a programmed interval which is initiated by sense or pace occurring in the synchronized chamber during which paces to the synchronized chamber are inhibited. For example, if the right ventricle is the rate chamber and the left ventricle is the synchronized chamber, a left ventricular protection period LVPP is triggered by a left ventricular sense which inhibits a left ventricular pace which would otherwise occur before the escape interval expires. The SCPP may be adjusted dynamically as a function of heart rate and may be different depending upon whether it was initiated by a sense or a pace. The SCPP provides a means to inhibit pacing of the synchronized chamber when a pace might be delivered during the vulnerable period or when it might compromise pumping efficiency by pacing the chamber too close to an intrinsic beat. In the case of a triggered mode where a synchronized chamber sense triggers a pace to the synchronized chamber, the pacing mode may be programmed to ignore the SCPP during the triggered pace. Alternatively, the mode may be programmed such that the SCPP starts only after a specified delay from the triggering event, which allows triggered pacing but prevents pacing during the vulnerable period.

In the case of synchronized chamber-only synchronized pacing, a synchronized chamber pace may be inhibited if a synchronized chamber sense occurs within a protection period prior to expiration of the rate chamber escape interval. Since the synchronized chamber pace is inhibited by the protection period, the rate chamber is not pseudo-paced and, if no intrinsic activity is sensed in the rate chamber, it will be paced upon expiration of the rate chamber escape intervals. The rate chamber pace in this situation may thus be termed a safety pace. For example, in left ventricle-only synchronized pacing, a right ventricular safety pace is delivered if the left ventricular pace is inhibited by the left ventricular protection period and no right ventricular sense has occurred.

As noted above, synchronized pacing may be applied to multiple sites in the same or different chambers. The synchronized pacing modes described above may be implemented in a multi-site configuration by designating one sensing/pacing channel as the rate channel for sensing/pacing a rate site, and designating the other sensing/pacing channels in either the same or the contralateral chamber as synchronized channels for sensing/pacing one or more synchronized sites. Pacing and sensing in the rate channel then follows rate chamber timing rules, while pacing and sensing in the synchronized channels follows synchronized chamber timing rules as described above. The same or different synchronized pacing modes may be used in each synchronized channel.

4. Maintaining Synchronized Pacing

Figure 2:
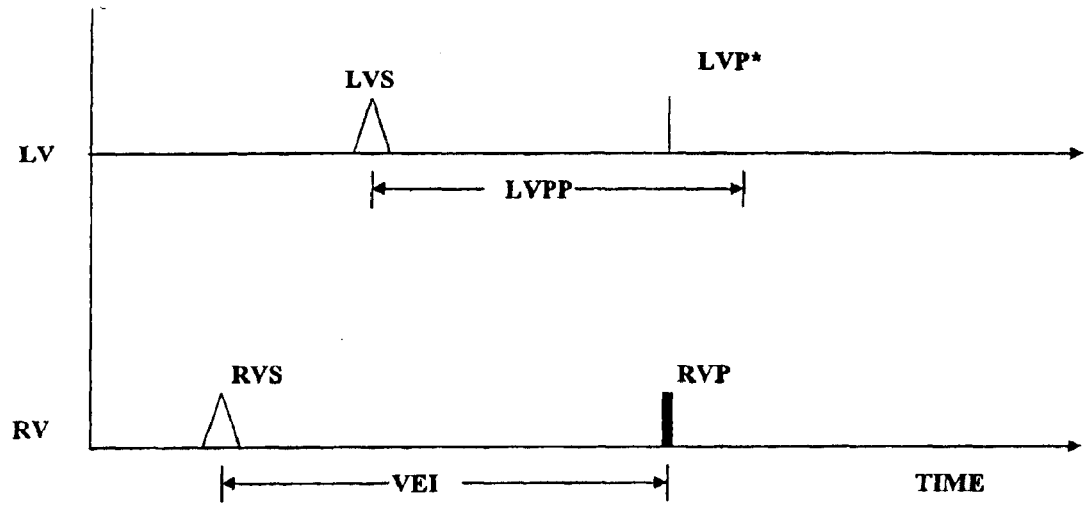
FIGS. 2 illustrates the operation of a synchronized chamber protection period.

The present invention provides a means for maintaining synchronized pacing during certain cardiac cycles when such pacing would otherwise be inhibited by a synchronized chamber protection period. FIG. 2 illustrates the situation where resynchronization is inhibited. Shown are timelines representing events occurring in the right and left ventricular sensing/pacing channels, designated RV and LV, respectively. A ventricular escape interval VEI, which could be either the lower rate limit interval or the atrio-ventricular delay interval following an atrial sense or pace, is shown as beginning at some earlier time. A left ventricular sense LVS occurs sometime during the ventricular escape interval VEI and initiates a left ventricular protection period LVPP. When the ventricular escape interval expires, a right ventricular pace RVP is delivered. Because the left ventricular protective period has not yet ended, however, no left ventricular pace is simultaneously delivered, as shown by the left ventricular pseudo-pace LVP* which represents the pacing algorithm's marking of the pacing instant where the pace would otherwise have occurred.

In accordance with the invention, when a pace to a synchronized chamber or site is scheduled during a synchronized chamber protection period, the pace is delayed for a protective delay period. The protective delay period may either be a specified fixed value or an automatically adjustable value that delays the pace only enough so that it occurs after the synchronized chamber protective period ends. In the latter case, a specified maximum limit may be placed on how much the pace can be delayed.

Figure 3A:
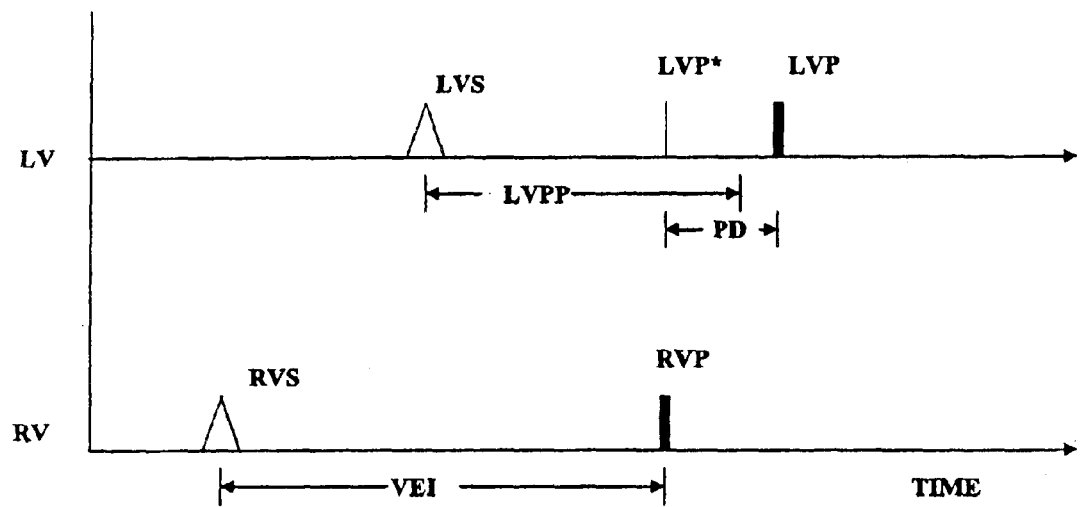
FIGS. 3A–C illustrate a protective delay interval used with biventricular pacing modes.

In one exemplary embodiment, the protective delay is used in a bilateral offset synchronized pacing mode. The protective delay in this case may be implemented as an adjustment to the synchronized chamber offset interval. Thus, when the synchronized chamber pace is scheduled during the chamber's protection period, the offset is increased by an amount equal to the delay period. FIG. 3A illustrates this embodiment in a biventricular offset pacing mode where the left ventricle is the synchronized chamber and the right ventricle is the rate chamber. The mode uses a zero offset so that normally the ventricles are paced simultaneously. The left ventricular sense LVS in this example occurs later than normal with respect to the right ventricular sense RVS. Such a situation commonly occurs in patients with left bundle branch block where intrinsic excitation is conducted more slowly to the left ventricle than to the right. A premature ventricular contraction originating in the right ventricle can produce a similar pattern. The left ventricular sense triggers the left ventricular protection period LVPP. After expiration of the ventricular escape interval, a right ventricular pace RVP is delivered, but the left scheduled ventricular pace is inhibited as shown by the left ventricular pseudo-pace LVP*. Instead, a left ventricular pace LVP is delivered at an instant delayed by a specified protective delay period PD so as to fall outside of the left ventricular protection period.

Figure 3B:
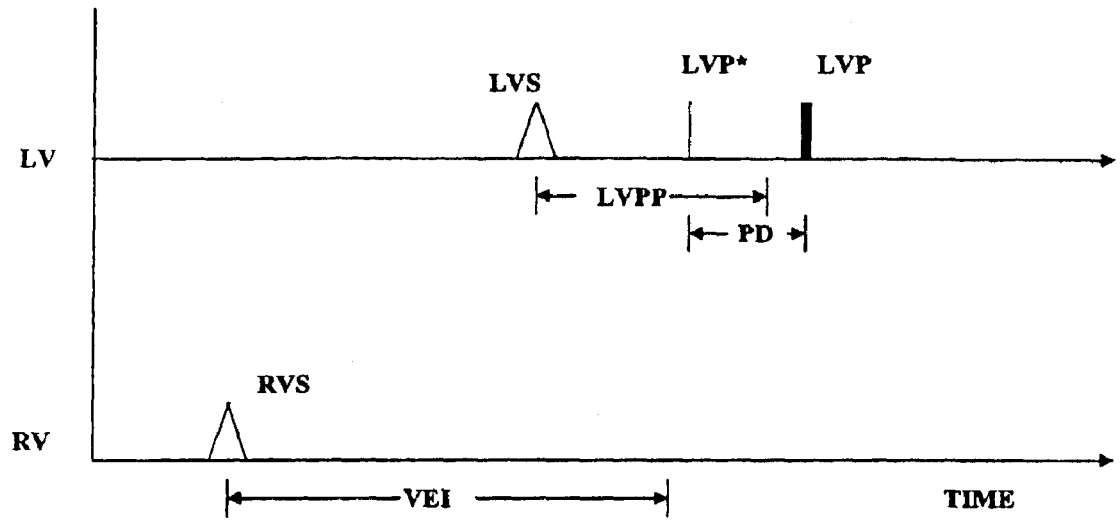

FIG. 3B shows how the protective delay period can be used in left ventricle-only synchronized pacing. A left ventricular pace LVP is delayed by the protective delay period PD and occurs outside of a left ventricular protection period triggered by a previous right ventricular sense. Here, delaying the pace allows a desired left ventricular pace to be delivered during the cardiac cycle when it would otherwise be inhibited. The protective delay may be used instead of, or in addition to, a right ventricular pace delivered during left ventricle-only synchronized pacing as described above.

Figure 3C:
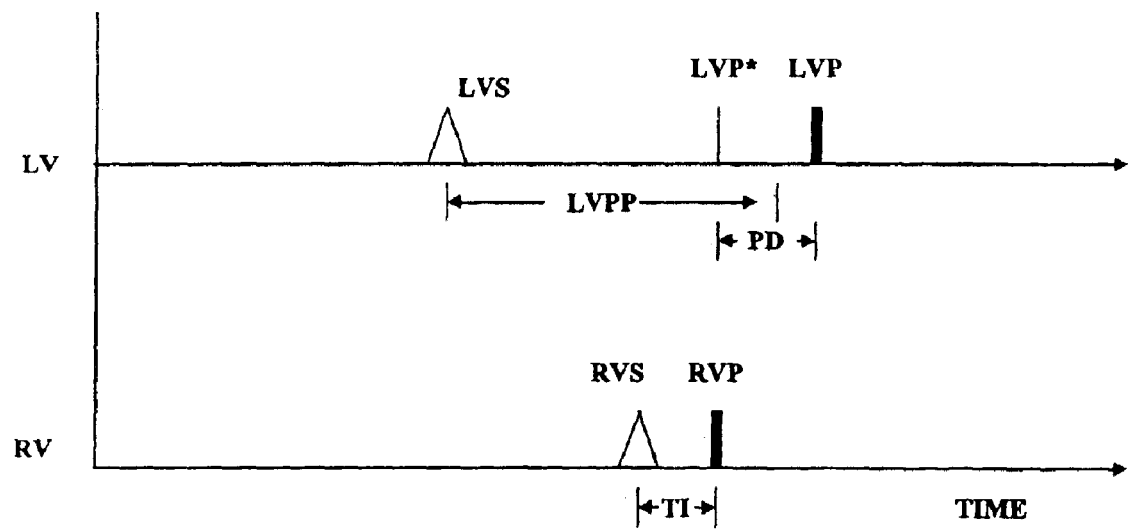

FIG. 3C illustrates the protective delay period as implemented with a ventricular triggered synchronized pacing mode. A left ventricular sense LVS occurs and initiates the left ventricular protection period LVPP. During the LVPP, a right ventricular sense RVS occurs which triggers both a right ventricular and a left ventricular pacing instant. The right ventricular pace RVP is delivered, but, because the left ventricular protection period has not yet ended, the left ventricular pace is delayed by the protective delay interval and occurs after the left ventricular protection period has ended.

The above examples employ a fixed protective delay interval so that a left ventricular pace is always delayed by the same amount when it would have occurred at any time within the left ventricular protection period. In alternate embodiments, a variable protective delay period can be used where a left ventricular pace is delayed only by the amount needed for the delayed pace to fall outside of the left ventricular protection period. A limit can be placed on the variable protective delay interval so that the pace can be delayed only by a specified maximum amount. If the left ventricular pace is maximally delayed, the delayed left ventricular pace will be inhibited if the left ventricular protective period has not yet ended.

The above-described embodiments dealt with ventricular synchronized pacing modes in which the right and left ventricles were designated as the rate and synchronized chambers, respectively. Embodiments may similarly be constructed in which other heart chambers are designated as the rate and synchronized chambers or in which a plurality of synchronized channels are utilized to provide synchronized pacing to multiple sites of a single chamber. In the latter situation, a separate protective delay period may be provided for each synchronized channel which delays pacing to a synchronized pacing site when a scheduled pace would otherwise be inhibited by a synchronous site protection period.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for operating a cardiac rhythm management device, comprising:

sensing cardiac chambers designated as a rate chamber and a synchronized chamber through separate channels and generating sense signals upon detection of depolarization occurring in a chamber;

pacing the synchronized chamber upon expiration of an escape interval which is reset by a rate chamber sense and by a synchronized chamber pace, and wherein pacing of the synchronized chamber is inhibited during a synchronized chamber protective period that is initiated by a synchronized chamber sense; and, delaying a pace to the synchronized chamber by a protective delay interval when the pace would otherwise occur within the synchronized chamber protective period.

2. The method of claim 1 wherein the synchronized chamber is also paced when triggered by a rate chamber sense unless the synchronized chamber pace would be delivered within the synchronized chamber protection period beginning after receipt of a synchronized chamber pace or sense, in which case the synchronized chamber pace is delayed by the protective delay interval.

3. The method of claim 1 wherein right and left ventricles are the rate and synchronized chambers, respectively, and the synchronized chamber protective period is a left ventricular protective period.

4. The method of claim 1 wherein the protective delay interval is a fixed value.

5. The method of claim 1 wherein the protective delay interval is a variable interval that delays the synchronized site pace only enough to fall outside of the synchronized site protective period.

6. The method of claim 1 wherein the variable protective delay interval is limited to a specified maximum value.

7. The method of claim 1 wherein the delayed synchronized site pace is inhibited if it would still fall within the synchronized site protective period.

8. The method of claim 1 wherein a rate chamber pace is delivered if the synchronized chamber pace is inhibited.

9. A cardiac rhythm management device, comprising:

sensing channels for sensing cardiac chambers designated as a rate chamber and a synchronized chamber and generating sense signals upon detection of depolarization occurring in a chamber;

a synchronized chamber pacing channel for delivering paces to the synchronized chamber;

a controller for controlling the delivery of paces in accordance with a programmed pacing mode; and, wherein the controller is programmed to pace the synchronized chamber upon expiration of an escape interval which is reset by a rate chamber sense or a synchronized chamber pace, to inhibit pacing of the synchronized chamber during a synchronized chamber protective period that is initiated by a synchronized chamber sense, and to delay a pace to the synchronized chamber by a protective delay interval when the pace would otherwise occur within the synchronized chamber protection period.

10. The device of claim 9 wherein right and left ventricles are the rate and synchronized chambers, respectively, and the synchronized chamber protective period is a left ventricular protective period.

11. The device of claim 9 further comprising a rate chamber pacing channel and wherein the controller is programmed to pace the rate chamber if the synchronized chamber pace is inhibited.

12. The device of claim 9 wherein the controller is programmed to also pace the synchronized chamber when triggered by a rate chamber sense unless the synchronized chamber pace would be delivered within the synchronized chamber protection period beginning after receipt of a synchronized chamber pace or sense, in which case the synchronized chamber pace is delayed by the protective delay interval.

13. The device of claim 9 wherein the protective delay interval is a fixed value.

14. The device of claim 9 wherein the protective delay interval is a variable interval that delays the synchronized site pace only enough to fall outside of the synchronized site protective period.

15. The device of claim 9 wherein the variable protective delay interval is limited to a specified maximum value.

16. The device of claim 9 wherein the delayed synchronized site pace is inhibited if it would still fall within the synchronized site protective period.

17. A cardiac rhythm management device, comprising:

means for sensing cardiac chambers designated as a rate chamber and a synchronized chamber through separate channels and generating sense signals upon detection of depolarization occurring in a chamber;

means for pacing the synchronized chamber upon expiration of an escape interval which is reset by a rate chamber sense and by a synchronized chamber pace, and wherein pacing of the synchronized chamber is inhibited during a synchronized chamber protective period that is initiated by a synchronized chamber sense; and, means for delaying a pace to the synchronized chamber by a protective delay interval when the pace would otherwise occur within the synchronized chamber protective period.

18. The device of claim 17 further comprising means for pacing the synchronized chamber when triggered by a rate chamber sense unless the synchronized chamber pace would be delivered within the synchronized chamber protection period beginning after receipt of a synchronized chamber pace or sense, in which case the synchronized chamber pace is delayed by the protective delay interval.

19. The device of claim 17 further comprising means pacing the rate chamber if the synchronized chamber pace is inhibited.

20. The device of claim 17 wherein right and left ventricles are the rate and synchronized chambers, respectively, and the synchronized chamber protective period is a left ventricular protective period.

* * * * *